(12) United States Patent
Muyari et al.

(10) Patent No.: US 11,096,714 B2
(45) Date of Patent: Aug. 24, 2021

(54) ENDOSCOPIC TREATMENT TOOL (71) Applicant: Olympus Corporation, Hachioji (JP)

(72) Inventors: Yuta Muyari, Hino (JP); Akane Yasukawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 55 days.

(21) Appl. No.: 16/699,947

(22) Filed: Dec. 2, 2019

(65) Prior Publication Data

US 2020/0100807 A1 Apr. 2, 2020

Related U.S. Application Data (63) Continuation of application No. PCT/JP2018/015860, filed on Apr. 17, 2018.

(30) Foreign Application Priority Data

Jun. 13, 2017 (JP) .............................. JP2017-115905

(51) Int. Cl.
*A61B 17/3205* (2006.01)
*A61B 18/12* (2006.01)
(Continued)

(52) U.S. Cl.
CPC .... *A61B 17/32056* (2013.01); *A61B 18/1206* (2013.01); *A61B 2017/0034* (2013.01);
(Continued)

(58) Field of Classification Search
CPC .... A61B 17/32056; A61B 2017/00358; A61B 2017/2212; A61B 2018/141
See application file for complete search history.

(56) References Cited

U.S. PATENT DOCUMENTS 4,202,338 A * 5/1980 Bitrolf .................. A61B 18/14
606/47
5,059,199 A * 10/1991 Okada .................. A61B 17/221
606/127
(Continued)

FOREIGN PATENT DOCUMENTS

JP H08-071082 A 3/1996
JP H8-299349 A 11/1996
(Continued)

OTHER PUBLICATIONS

Jul. 10, 2018 International Search Report issued in Application No. PCT/JP2018/015860.
(Continued)

*Primary Examiner* — Ryan J. Severson
(74) *Attorney, Agent, or Firm* — Oliff PLC (57) ABSTRACT

An endoscopic treatment tool comprises an elongated sheath and an elongated portion configured to be inserted in the elongated sheath and capable of being movable back and forth in directions. A loop portion is disposed on a distal end of the elongated portion and is constructed of a wire folded to form into a loop. The loop portion includes a first bent portion, a pair of second bent portions, a pair of third bent portions, and a fourth bent portion all of which are integrally formed from a distal end toward a proximal end of the loop portion. A first length that represents a length from the first bent portion to the fourth bent portion in the directions along the longitudinal axis ranges from one and half times to two times a first width that represents a maximum dimension of the loop portion in directions perpendicular to the longitudinal axis.

7 Claims, 8 Drawing Sheets (51) Int. Cl.
    *A61B 17/00*    (2006.01)
    *A61B 17/221*   (2006.01)
    *A61B 18/00*    (2006.01)
    *A61B 18/14*    (2006.01)

(52) U.S. Cl.
    CPC ............... *A61B 2017/00358* (2013.01); *A61B 2017/00862* (2013.01); *A61B 2017/2212* (2013.01); *A61B 2018/00077* (2013.01); *A61B 2018/00178* (2013.01); *A61B 2018/141* (2013.01)

(56) References Cited

U.S. PATENT DOCUMENTS

| | | | |
|---|---|---|---|
| 6,224,611 | B1 | 5/2001 | Ouchi |
| 7,270,663 | B2* | 9/2007 | Nakao ................. A61B 17/221 606/47 |
| 10,226,267 | B2* | 3/2019 | Muyari ................ A61B 17/221 |
| 10,478,044 | B2* | 11/2019 | Yanuma ............... A61B 1/00098 |
| 10,667,838 | B2* | 6/2020 | Uspenski ......... A61B 17/32056 |
| 2002/0091394 | A1* | 7/2002 | Reynolds ............. A61B 17/221 606/127 |
| 2005/0085808 | A1 | 4/2005 | Nakao |
| 2015/0342633 | A1 | 12/2015 | Yanuma et al. |
| 2017/0224365 | A1 | 8/2017 | Muyari et al. |
| 2020/0100807 | A1* | 4/2020 | Muyari ............ A61B 17/32056 |

FOREIGN PATENT DOCUMENTS

| | | |
|---|---|---|
| JP | H11-123198 A | 5/1999 |
| JP | 2000-083963 A | 3/2000 |
| JP | 2000-083964 A | 3/2000 |
| JP | 2001-292960 A | 10/2001 |
| JP | 2010-505450 A | 2/2010 |
| JP | 2015-008827 A | 1/2015 |
| WO | 2008/044615 A1 | 4/2008 |
| WO | 2016/147471 A1 | 9/2016 |

OTHER PUBLICATIONS

Jul. 10, 2018 Written Opinion of the International Search Authority issued in Application No. PCT/JP2018/015860.

* cited by examiner

(Prior Art)

ENDOSCOPIC TREATMENT TOOL

CROSS-REFERENCE TO RELATED APPLICATIONS

This application is a continuation application of PCT Application No. PCT/JP2018/015860 filed on Apr. 17, 2018, which in turn claim priority to the Japanese Patent Application No. 2017-115905 filed on Jun. 13, 2017 in Japan which is hereby incorporated by reference in its entirety.

TECHNICAL FIELD

The disclosed Technology relates to an endoscopic treatment tool.

DESCRIPTION OF THE RELATED ART

Heretofore, in the medical field or the like, there have been used snares as an endoscopic treatment tool for excising tissues such as polyps in digestive tracts through endoscopes. Generally, an endoscopic snare includes a sheath, an operating wire axially movably inserted in the sheath, and a snare loop made of a resilient wire coupled to the operating wire. The snare loop is formed by folding a single resilient wire back over itself at a position corresponding to the distal end of the snare loop. When the operating wire is axially moved back and forth, the snare loop goes into and out of the distal end of the sheath. The snare loop as it projects out of the distal end of the sheath spreads open to a width that increases under its own resiliency. The snare loop as it is pulled back into the sheath is contracted.

When an endoscopic snare is used on a patient's body, the surgeon inserts the snare into the body through an endoscope until the snare reaches a position near a tissue as a target to be excised, e.g., a polyp on a digestive tract. Then, the surgeon places the snare loop around the root of the tissue to be excised and pulls the operating wire toward a proximal-end side thereof. Part of the snare loop is pulled into the sheath, reducing the width of the opening thereof. As a result, the tissue is tightened and excised from the digestive tract by the snare loop.

According to the related art, however, when the surgeon pulls the operating wire toward the proximal-end side to pull the snare loop into the sheath, the width of the opening of the snare loop is often reduced abruptly. For example, when the surgeon starts to pull the operating wire toward the proximal-end side, the width of the opening of the snare loop may abruptly decrease to one-half or 40% or less of the maximum width of the opening thereof.

Japanese Patent Application JP Hei 11-123198A (PTL 1) discloses an endoscopic snare having a snare loop that includes a first main bent portion, a second main bent portion, and a third main bent portion that are successively arranged from the distal-end side of the snare loop. The snare loop is of a hexagonal shape. The snare loop of the endoscopic snare disclosed in PTL 1 has its proximal-end side bound by a joint pipe and inserted in a sheath so as to be movable back and forth.

Figure 9:
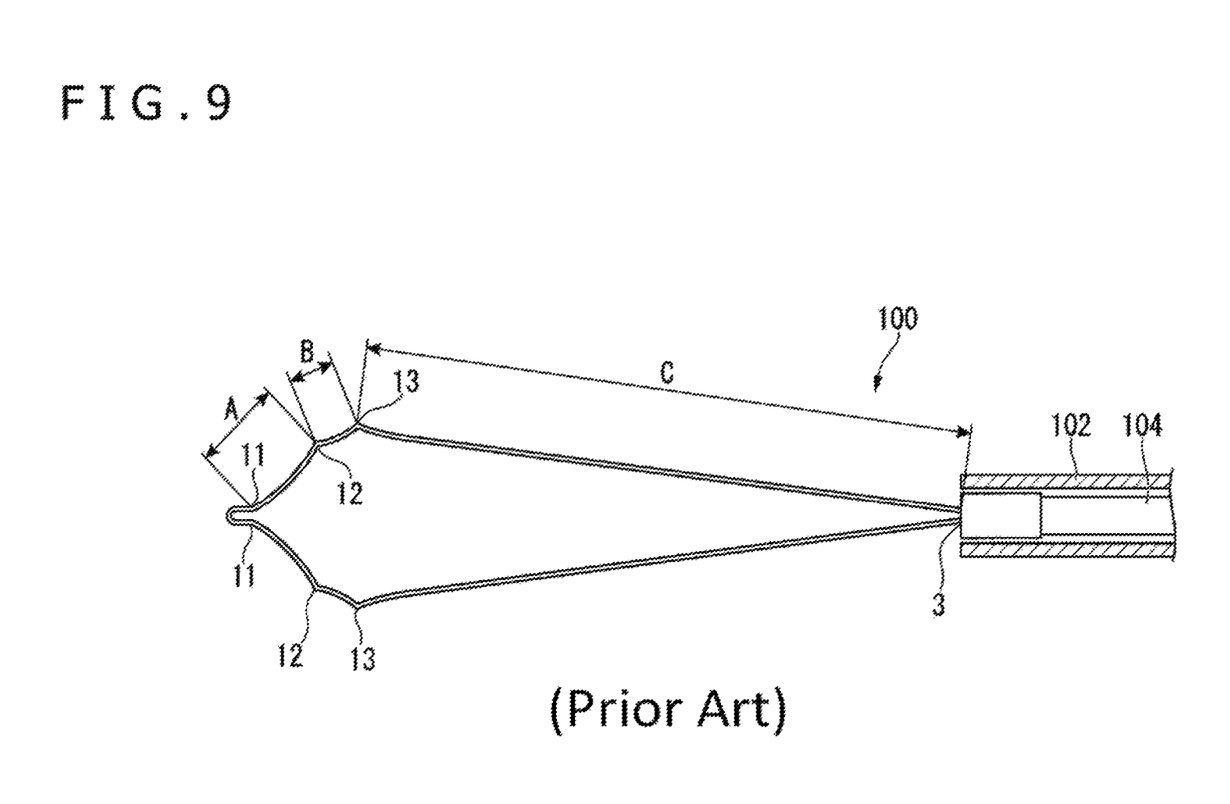
FIG. 9 is a view illustrating the structure of a prior art endoscopic snare.

As illustrated in FIG. 9 of the accompanying drawings, the snare loop, denoted by 100, of the endoscopic snare disclosed in PTL 1 has a length A from the first main bent portion, denoted by 11, to the second main bent portion, denoted by 12, a length B from the second main bent portion 12 to the third main bent portion, denoted by 13, and a length C from the third main bent portion 13 to a bound rear end portion 3. Of these lengths, the length C from the third main bent portion 13 to the bound rear end portion 3 is the longest. More specifically, the snare loop 100 of the endoscopic snare disclosed in PTL 1 is formed such that the length A is in the range of two times to three times the length B and the length C is in the range of five times to ten times the length A. The endoscopic snare disclosed in PTL 1 is capable of catching and excising small to large polyps by adjusting the size of the snare loop 100.

Figure 10:
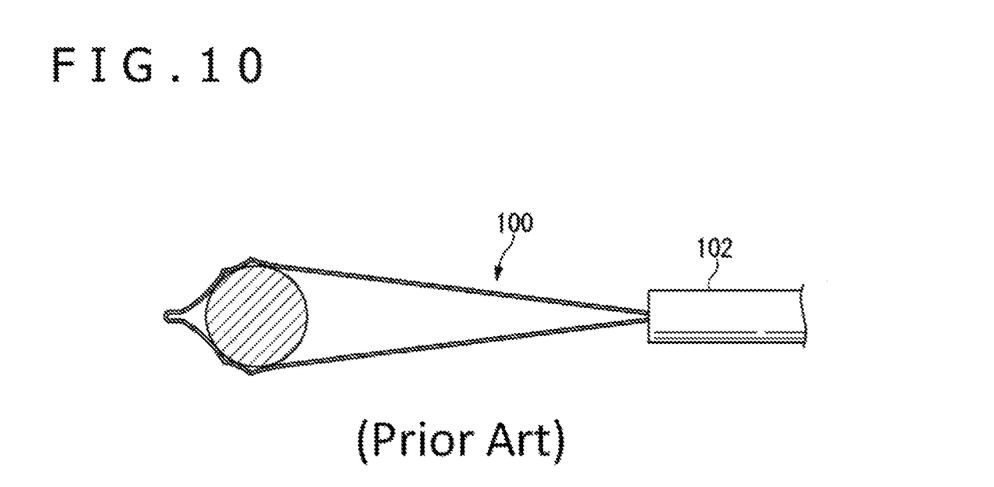
FIG. 10 a view illustrating the manner in which the prior art existing endoscopic snare operates when it is in use.

In treating a large polyp using the endoscopic snare disclosed in PTL 1, when the surgeon protrudes the snare loop 100 of the endoscopic snare from the distal end of the sheath, denoted by 102, the snare loop 100 expands largely under its own resiliency, as illustrated in FIG. 10 of the accompanying drawings. The surgeon can then place the snare loop 100 around the polyp to catch the polyp. At this time, since the length C from the third main bent portion 13 to the bound rear end portion 3 of the snare loop is long, the snare loop 100 has a large entire length and a gradually spreading profile. As a consequence, the width of the opening of the snare loop 100 changes relatively gradually as the surgeon operates the snare loop 100. However, since the entire length of the snare loop 100 is large, a normal tissue other than the target to be excised may enter the snare loop 100. As a result, the normal tissue not to be excised as well as the tissue as the target to be excised may possibly be excised by the operation of the surgeon.

For treating a small polyp whose diameter is of approximately 3 mm using the endoscopic snare disclosed in PTL 1, the surgeon needs to adjust the size of the snare loop 100 by pulling the operating wire 104 to the proximal-end side of the sheath 102. However, while the size of the snare loop 100 is being adjusted, since the entire length of the snare loop 100 is large, much of a normal tissue not to be excised may possibly enter the snare loop 100 in the process.

Accordingly, there is a need for an endoscopic that allows a snare loop to be adjusted and excise a targeted tissue without entangling a normal tissue within the snare loop.

BRIEF SUMMARY OF EMBODIMENTS

One aspect of the disclosed technology is directed to an endoscopic treatment tool comprises an elongated sheath and an elongated portion configured to be inserted in the elongated sheath and capable of being movable back and forth in directions along a longitudinal axis of the sheath. A loop portion is disposed on a distal end of the elongated portion and is constructed of a wire folded to form into a loop. The loop is variable in a size and a shape when the loop portion is moved into and out of the elongated sheath as the elongated portion being moved back and forth. The loop portion includes a first bent portion, a pair of second bent portions, a pair of third bent portions, and a fourth bent portion all of which are integrally formed from a distal end toward a proximal end of the loop portion. The pair of third bent portions and the fourth bent portion are joined to one another by proximal-end wire portions. The first bent portion and the pair of second bent portions are joined to one another by distal-end wire portions and in which length of the proximal-end wire portions is larger than length of the distal-end wire portions. The pair of second bent portions and the pair of third bent portions are joined to one another by intermediate wire portions and the length of the distal-end wire portions is larger than length of the intermediate wire portions. The loop portion projects maximally from the sheath when the elongated portion is moved back and forth. A first length that represents a length from the first bent portion to the fourth bent portion in the directions along the longitudinal axis ranges from one and half times to two times a first width that represents a maximum dimension of the loop portion in directions perpendicular to the longitudinal axis. The length of the proximal-end wire portions ranges from 40% to 60% of the first length and the length of the intermediate wire portions ranges from 20% to 30% of the first width of the loop portion.

Another aspect of the disclosed technology is directed to an endoscopic treatment tool comprises an elongated sheath and an elongated portion configured to be inserted in the elongated sheath and capable of being movable back and forth in directions along a longitudinal axis of the elongated sheath. The loop portion is disposed on a distal end of the elongated portion and constructed of a wire folded to form into a loop. The loop being variable in a size and a shape when the loop portion being moved into and out of the sheath as the elongated portion being moved back and forth. The loop portion includes a first bent portion, a pair of second bent portions, a pair of third bent portions, and a fourth bent portion all of which being integrally formed from a distal end toward a proximal end of the loop portion. The pair of third bent portions and the fourth bent portion are joined to one another by proximal-end wire portions. The first bent portion and the pair of second bent portions are joined to one another by distal-end wire portions and length of the proximal-end wire portions is larger than length of the distal-end wire portions. The pair of second bent portions and the pair of third bent portions are joined to one another by intermediate wire portions and the length of the distal-end wire portions is larger than length of the intermediate wire portions and the loop portion projects maximally from the sheath and when the elongated portion is moved back and forth. The length of the proximal-end wire portions ranges from 40% to 60% of a first length and when a portion of the loop portion which has ⅔ of the first length projects from the sheath, a dimension of the loop portion in directions perpendicular to the longitudinal axis ranges from 40% to 60% exclusive of the first width of the loop portion.

A further aspect of the disclosed technology is directed to an endoscopic treatment tool comprises an elongated sheath. An elongate portion configured to be inserted in the elongated sheath and capable of being movable back and forth in directions along a longitudinal axis of the sheath. A loop portion is disposed on a distal end of the elongated portion and constructed of a wire folded to form into a loop. The loop is variable in a size and a shape when the loop portion being moved into and out of the sheath as the elongated portion being moved back and forth. The loop portion includes a first bent portion, a pair of second bent portions, a pair of third bent portions, and a fourth bent portion all of which being integrally formed from a distal end toward a proximal end of the loop portion. The pair of third bent portions and the fourth bent portion are joined to one another by proximal-end wire portions. The first bent portion and the pair of second bent portions are joined to one another by distal-end wire portions and length of the proximal-end wire portions is larger than length of the distal-end wire portions. The pair of second bent portions and the pair of third bent portions are joined to one another by intermediate wire portions and the length of the distal-end wire portions is larger than length of the intermediate wire portions. The loop portion projects maximally from the sheath and when the elongated portion is moved back and forth, the length of the proximal-end wire portions ranges from 40% to 60% of a first length and in the loop portion, a distal-end bend angle is formed between the distal-end wire portions and the intermediate wire portions is smaller than a proximal-end side bend angle formed between the intermediate wire portions and the proximal-end wire portions.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

It is an object of the disclosed Technology to provide an endoscopic treatment tool that allows the width of the opening of a snare loop thereof to be adjusted finely and that can excise a tissue as a target to be excised in an appropriate excision range and by an appropriate excision amount.

An endoscopic treatment tool according to an embodiment of the disclosed Technology will hereinafter be described with reference to FIGS. 1 through 5.

Structure of Endoscopic Treatment Tool 1

Figure 1:
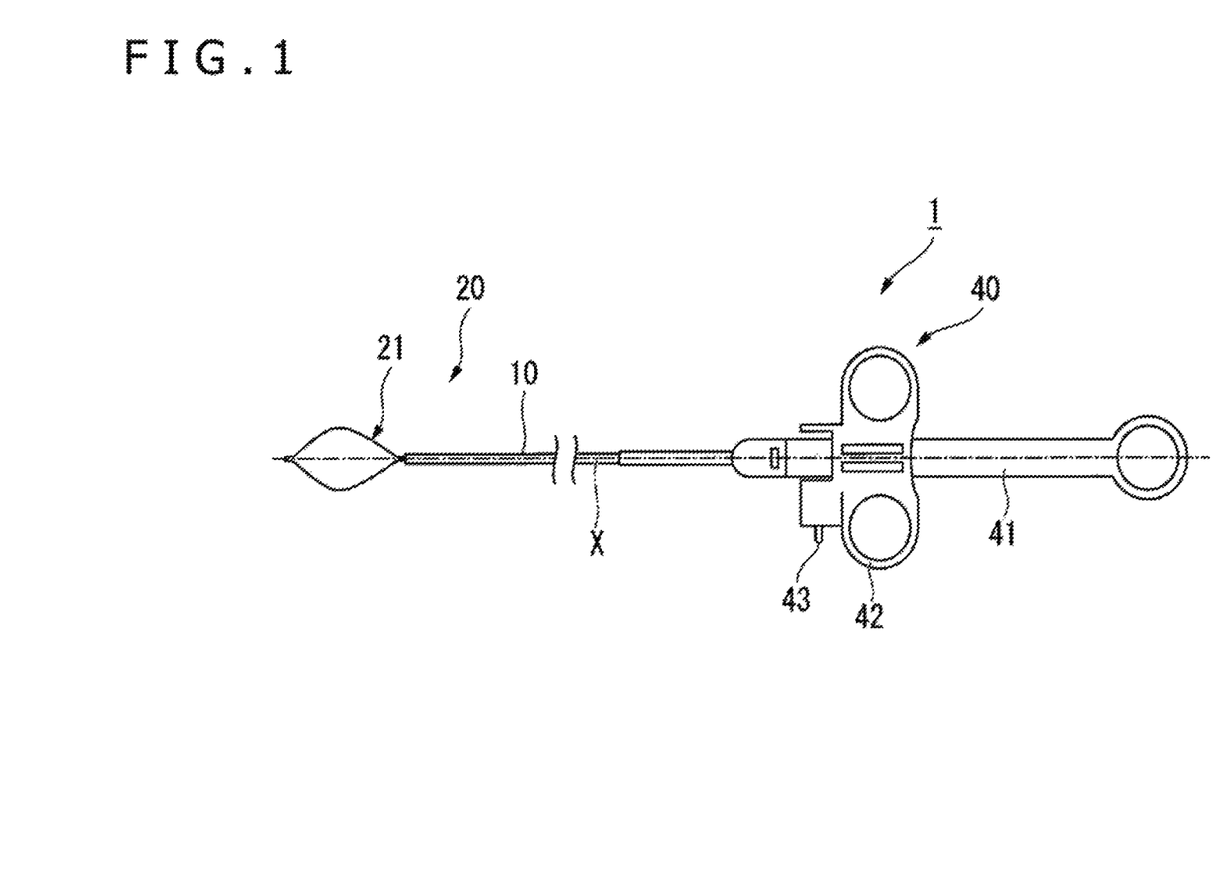
FIG. 1 is a view illustrating the overall structure of an endoscopic treatment tool according to an embodiment of the disclosed Technology.
Figure 2A:
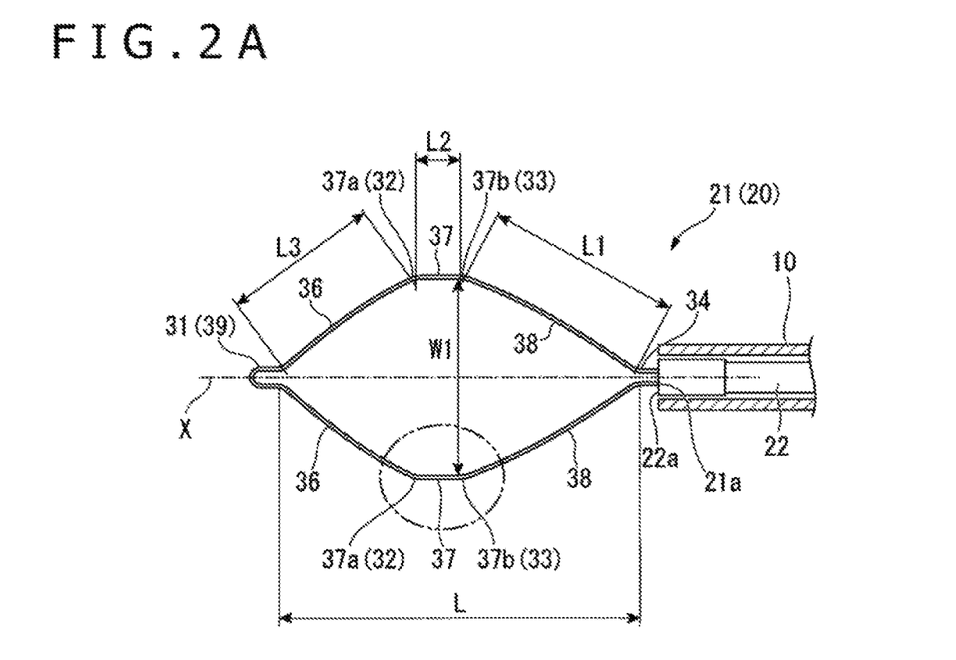
FIG. 2A is a view illustrating the structure of a snare loop of the endoscopic treatment tool according to the embodiment of the disclosed Technology.
Figure 2B:
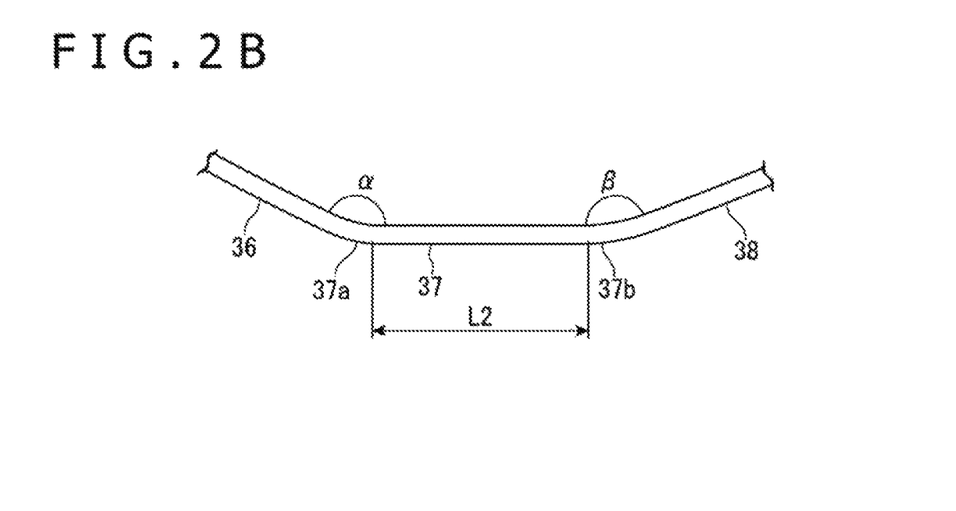
FIG. 2B is an enlarged view illustrating a portion of the structure of the snare loop illustrated in FIG. 2A.
Figure 3:
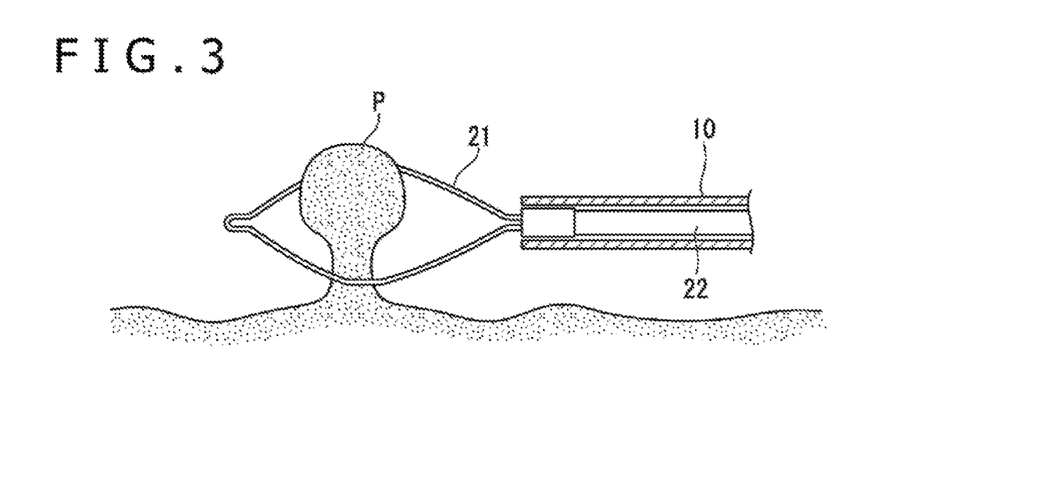
FIG. 3 is a view illustrating the manner in which the endoscopic treatment tool according to the embodiment of the disclosed Technology operates when it is in use.
Figure 4:
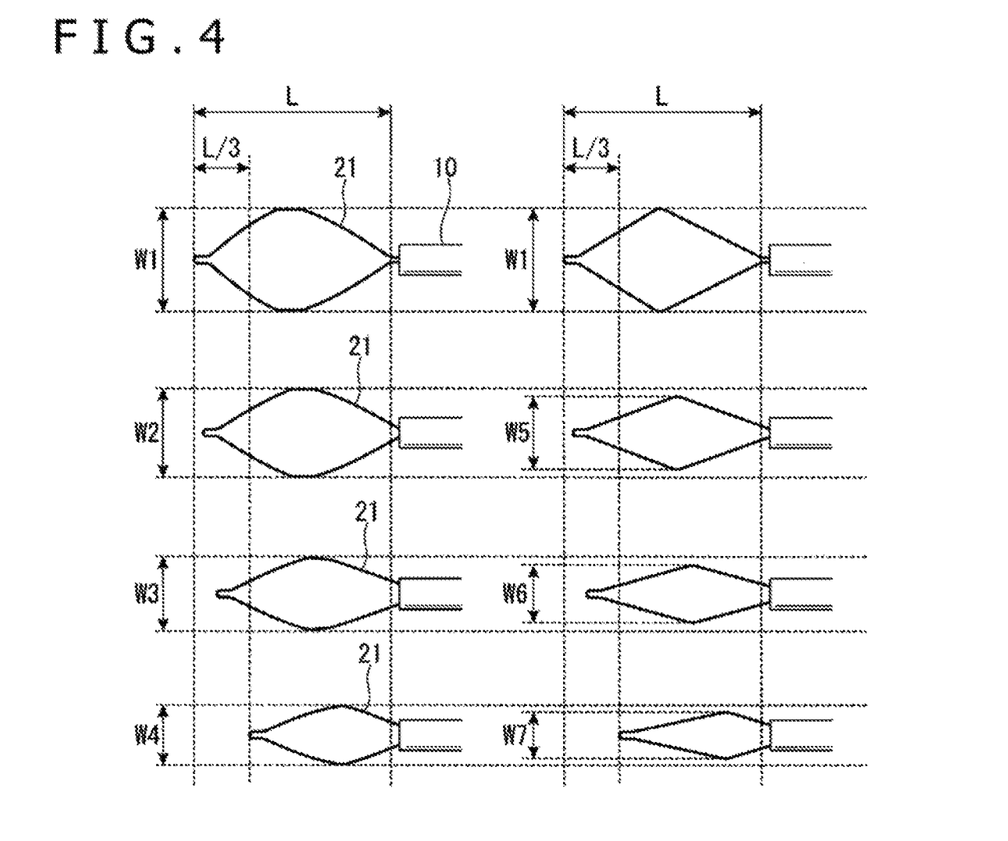
FIG. 4 is a view illustrating the manner in which the endoscopic treatment tool according to the embodiment of the disclosed Technology operates to pull part of the snare loop into a sheath.
Figure 5:
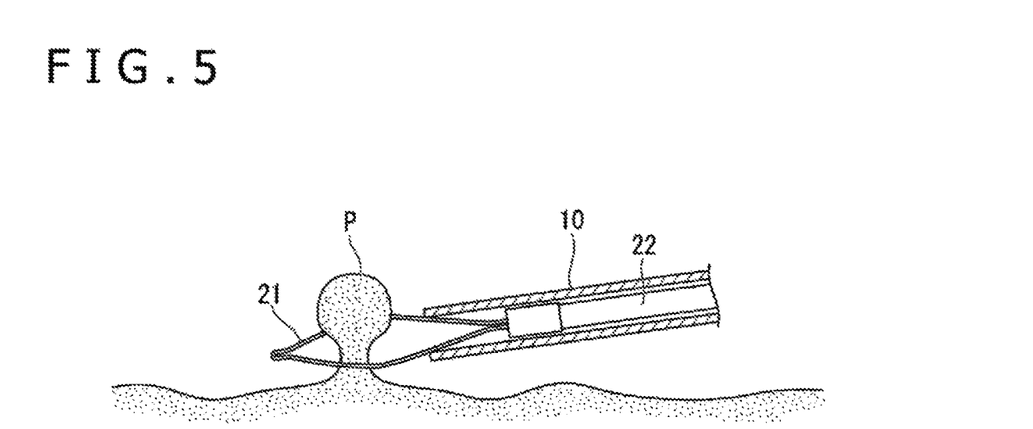
FIG. 5 is a view illustrating the manner in which the endoscopic treatment tool according to the embodiment of the disclosed Technology operates when it is in use.

FIG. 1 is a view illustrating the overall structure of the endoscopic treatment tool according to the present embodiment. FIG. 2A is a view illustrating the structure of a snare loop of the endoscopic treatment tool according to the present embodiment. FIG. 2B is an enlarged view illustrating a portion of the structure of the snare loop of the endoscopic treatment tool according to the present embodiment, the enlarged view illustrating a portion encircled by two-dot-and-dash line in FIG. 2A. FIG. 3 is a view illustrating the manner in which the endoscopic treatment tool according to the present embodiment operates when it is in use. FIG. 4 is a view illustrating the manner in which the endoscopic treatment tool according to the present embodiment operates to pull part of the snare loop into a sheath. FIG. 5 is a view illustrating the manner in which the endoscopic treatment tool according to the present embodiment operates when it is in use.

As illustrated in FIG. 1, the endoscopic treatment tool, denoted by 1, according to the present embodiment includes a sheath 10, a snare wire 20, and an operating portion 40.

The sheath 10 of the endoscopic treatment tool 1 extends along a longitudinal axis X and is elongated so as to be inserted into a body cavity. The sheath 10 is made of an insulative material, e.g., a fluororesin such as PTFE (polytetrafluoroethylene) or the like. The sheath 10 is flexible and can be inserted into and pulled out of a treatment tool channel, not illustrated, in an endoscope along the curved configuration of a lumen tissue or the like in the body cavity.

As illustrated in FIG. 2A, the snare wire 20 includes a loop portion 21 disposed on a distal-end side thereof and an operating wire, or elongate portion, 22 disposed on a proximal-end side thereof. The snare wire 20 is electrically conductive so that a high-frequency electric current can flow therethrough.

The snare wire 20 according to the present embodiment is formed by folding a single resilient wire, e.g., a stranded wire of stainless steel threads, back over itself, and hence can be repeatedly deformed. Therefore, the surgeon can perform an action to hold again a target to be excised using the snare wire 20 and an action to successively catch a plurality of different targets to be excised using the snare wire 20.

The snare wire 20 according to the present embodiment has a diameter of approximately 0.3 mm, for example, that is smaller than the diameter of 0.47 mm of existing snare wires dedicated to the use of high-frequency electric currents. Consequently, the surgeon can carry out a treatment for passing a high-frequency electric current through the snare wire 20 to excise a tissue and a treatment for tightening and excising a tissue with the snare wire 20 without passing a high-frequency electric current through the snare wire 20.

According to the present embodiment, the loop portion 21 on the distal-end side of the snare wire 20 is in the form of a loop having a substantially hexagonal shape that is symmetrical with respect to the longitudinal axis X of the sheath 10. The loop portion 21 has a first bent portion 31, a pair of second bent portions 32, a pair of third bent portions 33, and a fourth bent portion 34 that are successively arranged from the distal-end side to the proximal-end side. Each of the first bent portion 31, the pair of second bent portions 32, the pair of third bent portions 33, and the fourth bent portion 34 bent in projecting outwardly from the loop shape of the loop portion 21. The fourth bent portion 34 disposed at a proximal end 21a of the loop portion 21 is connected to a distal end 22a of the operating wire 22. The first bent portion 31 has a protrusion 39 formed by folding the resilient wire. The protrusion 39 of the loop portion 21 has its shape unchanged when the loop portion 21 is moved into and out of the opening in a distal end of the sheath 10. When the surgeon protrudes the loop portion 21 from the opening in the distal end of the sheath 10, the protrusion 39 acts against forces tending to push in the loop portion 21, allowing the loop portion 21 to open.

The loop portion 21 has a pair of distal-end wire portions 36, a pair of intermediate wire portions 37, and a pair of proximal-end wire portions 38 that are successively arranged from the distal-end side to the proximal-end side of the loop portion 21. The pair of distal-end wire portions 36 belong to regions of the snare wire 20 that are disposed between the first bent portion 31 and the pair of second bent portions 32. The pair of intermediate wire portions 37 belong to regions of the snare wire 20 that are disposed between the pair of second bent portions 32 and the pair of third bent portions 33. The pair of proximal-end wire portions 38 belong to regions of the snare wire 20 that are disposed between the pair of third bent portions 33 and the fourth bent portion 34. According to the present embodiment, the pair of intermediate wire portions 37 of the loop portion 21 lies substantially parallel to each other. According to the present embodiment, a length of the proximal-end wire portions 38 is defined as L1, a length of the intermediate wire portions 37 as L2, and a length of the distal-end wire portions 36 as L3.

The intermediate wire portions 37 of the loop portion 21 of the endoscopic treatment tool 1 according to the present embodiment have distal-end portions 37a and proximal-end portions 37b. The distal-end portions 37a of the intermediate wire portions 37 function as junctions between the intermediate wire portions 37 and the distal-end wire portions 36. The proximal-end portions 37b of the intermediate wire portions 37 function as junctions between the intermediate wire portions 37 and the proximal-end wire portions 38.

As illustrated in FIG. 2A, when the endoscopic treatment tool 1 according to the present embodiment is in use, the loop portion 21 projects outwardly completely from the opening in the distal end of the sheath 10. At this time, as a result of the loop portion 21 spreading itself under the resiliency of the resilient wire, the area of the loop shape of the loop portion 21 is maximum. In this state, the distance from the fourth bent portion 34 on the proximal-end side to the first bent portion 31 on the distal-end side of the loop portion 21 along the longitudinal axis X of the sheath 10 is defined as a length, or first length, L of the loop portion 21 in longitudinal-axis directions. When the loop portion 21 projects outwardly completely from the opening in the distal end of the sheath 10, the width of the opening of the loop portion 21 in directions perpendicular to the longitudinal axis X of the sheath 10 is defined as a maximum opening width, or first width, W1 of the loop portion 21. According to the present embodiment, since the pair of intermediate wire portions 37 of the loop portion 21 lie substantially parallel to each other, the maximum opening width W1 of the loop portion 21 is substantially equal to the distance between the pair of intermediate wire portions 37.

When the loop portion 21 projects completely from the opening in the distal end of the sheath 10, the length L of the loop portion 21 according to the present embodiment in the longitudinal-axis directions ranges from one and half times to two times the maximum opening width W1 of the loop portion 21.

According to the present embodiment, the length L1 of the proximal-end wire portions 38 is larger than the length L3 of the distal-end wire portions 36. The length L3 of the distal-end wire portions 36 is larger than the length L2 of the intermediate wire portions 37. In other words, in the loop portion 21 according to the present embodiment, the length L1 of the proximal-end wire portions 38, the length L2 of the intermediate wire portions 37, and the length L3 of the distal-end wire portions 36 satisfy the relationship: L1>L3>L2.

In the loop portion 21 according to the present embodiment, the length L1 of the proximal-end wire portions 38 ranges from 40% to 60% of the length L of the loop portion 21 in the longitudinal-axis directions, and the length L2 of the intermediate wire portions 37 ranges from 20% to 30% of the maximum opening width W1 of the loop portion 21.

The parts of the endoscopic treatment tool 1 according to the present embodiment may be appropriately selected according to the actual usage of the endoscopic treatment tool 1 insofar as the dimensional relationship described hereinbefore is satisfied. The parts of the loop portion 21 of the endoscopic treatment tool 1 according to the present embodiment may be formed with their dimensions variable in appropriate ranges according to the actual usage of and the manufacturing process for the endoscopic treatment tool 1.

According to the present embodiment, as illustrated in FIG. 2B, the distal-end wire portions 36 and the intermediate wire portions 37 are disposed next to each other and connected to each other. The distal-end wire portions 36 and the intermediate wire portions 37 that are disposed next to each other form a distal-end side bend angle α therebetween. Similarly, the intermediate wire portions 37 and the proximal-end wire portions 38 that are disposed next to each other form a proximal-end side bend angle β therebetween. In the loop portion 21 of the endoscopic treatment tool 1 according to the present embodiment, the distal-end side bend angle α is smaller than the proximal-end side bend angle β.

According to the present embodiment, the loop portion 21 has an intermediate position that may be disposed on the intermediate wire portions 37 along the directions of the longitudinal axis X of the sheath 10. Stated otherwise, a portion of the substantially hexagonal shape of the loop portion 21 where the length in the longitudinal-axis directions is ½ may be positioned on the intermediate wire portions 37.

As illustrated in FIG. 1, the operating portion 40 according to the present embodiment includes an operating portion body 41 connected to a proximal-end portion of the sheath 10, a slider 42 mounted on the operating portion body 41, and a connector 43.

The operating wire 22 is connected to the slider 42. Therefore, the snare wire 20 is moved back and forth with respect to the sheath 10 by moving the slider 42 back and forth with respect to the operating portion body 41. According to the present embodiment, when the slider 42 is advanced with respect to the operating portion body 41, the loop portion 21 projects outwardly from the opening in the distal end of the sheath 10. When the slider 42 is retracted with respect to the operating portion body 41, the loop portion 21 is progressively accommodated or retreated back into the sheath 10.

The connector 43 can be connected to a high-frequency power supply device, not illustrated, and is capable of supplying a high-frequency electric current to the operating wire 22. As the operating wire 22 is electrically connected to the loop portion 21, the high-frequency electric current supplied from the high-frequency power supply device is delivered through the operating wire 22 to the loop portion 21.

Operation of Endoscopic Treatment Tool 1

Next, operation of the endoscopic treatment tool 1 for excising a polyp P bulging from the epithelium of an organism using the endoscopic treatment tool 1 will be described hereinafter with reference to FIG. 3.

First, the surgeon inserts an endoscope into a patient's body cavity according to a known procedure, and guides the distal end of the endoscope to the position of the polyp P as a target to be excised, thereby catching the polyp P in the visual field of the endoscope. Then, the surgeon inserts the endoscopic treatment tool 1 according to the present embodiment into the endoscope. After protruding the endoscopic treatment tool 1 from the opening in the distal-end side of the endoscope, the surgeon slides the slider 42 of the operating portion 40 toward the distal-end side with respect to the operating portion body 41, as illustrated in FIG. 1. The operating wire 22 that is connected to the slider 42 is pushed and moved toward the distal-end side with respect to the sheath 10 until the loop portion 21 in its entirety projects outwardly from the opening in the distal-end side of the sheath 10. When the loop portion 21 in its entirety projects outwardly from the opening in the distal-end side of the sheath 10, the loop portion 21 spreads due to restoring forces under its own resiliency, and is deformed into a substantially hexagonal shape, as illustrated in FIG. 3 (first state).

In a case where the polyp P is large in size, e.g., approximately 10 mm across, the surgeon places the loop portion 21 around the polyp P in the first state. Then, the surgeon slides the slider 42 of the operating portion 40 toward the proximal-end side with respect to the operating portion body 41. As a result, the proximal-end side of the loop portion 21 is pulled into the sheath 10, causing the loop portion 21 to tighten the root of the polyp P.

After the root of the polyp P is tightened by the loop portion 21, the surgeon operates the high-frequency power supply device, not illustrated, to supply a high-frequency electric current to the endoscopic treatment tool 1. When the high-frequency electric current flows through the loop portion 21, the polyp P tightened by the loop portion 21 is excised while being cauterized.

As described hereinbefore, the snare wire 20 has a diameter of approximately 0.3 mm, for example, and hence is thin. Therefore, the surgeon may excise the polyp P by moving the loop portion 21 toward the proximal-end side while the root of the polyp P is being tightened by the loop portion 21, without causing the high-frequency electric current to flow through the loop portion 21.

In a case where the polyp P is small in size, e.g., approximately 5 mm across, the surgeon needs to adjust the loop portion 21 from the first state to a state in which the size of the loop shape of the loop portion 21 matches the size of the polyp P. As illustrated in a left side of FIG. 4, the surgeon slides the slider 42 of the operating portion 40 toward the proximal-end side with respect to the operating portion body 41, pulling part of the proximal-end side of the loop portion 21 into the sheath 10.

FIG. 4 illustrates in its left side the manner in which the endoscopic treatment tool 1 according to the present embodiment operates to pull the loop portion 21 of the snare wire 20 into the sheath 10. FIG. 4 illustrates in its right side the manner in which an existing endoscopic treatment tool operates to pull a loop portion of a snare wire that is free of the intermediate wire portions 37 into a sheath. As illustrated in the left side of FIG. 4, during the process in which part of the loop portion 21 of the endoscopic treatment tool 1 according to the present embodiment is pulled into the sheath 10, the opening width of the loop portion 21 become smaller in the order from a first width W1 to a second opening width, or second width, W2, to a third opening width, or third width, W3, to a fourth opening width, or fourth width, W4. On the other hand, as illustrated in the right side of FIG. 4, when the loop portion of the snare wire that is free of the intermediate wire portions 37 is pulled into the sheath, the opening width of the loop portion become smaller in the order from the first width W1 to a fifth opening width, or fifth width, W5, to a sixth opening width, or sixth width, W6, to a seventh opening width, or seventh width, W7.

As illustrated in FIG. 4, during the process in which the loop portion of the snare wire is pulled into the sheath, a comparison between the snare wire that is free of the intermediate wire portions 37 and the endoscopic treatment tool 1 according to the present embodiment indicates that the fifth width W5 is smaller than the second width W2, the sixth width W6 is smaller than the third width W3, and the seventh width W7 is smaller than the fourth width W4.

When the surgeon operates the operating wire 22 to adjust the opening width of the loop portion 21, as a result of the pair of distal-end wire portions 36, the pair of intermediate wire portions 37, and the pair of proximal-end wire portions 38 being pulled toward the proximal-end side into the sheath 10, the opening width of the loop shape of the loop portion 21 is reduced. During this process, the proximal-end portions 37b of the intermediate wire portions 37 become closer to the longitudinal axis X of the sheath 10 in the directions perpendicular to the longitudinal axis X while being moved toward the proximal-end side along the longitudinal axis X by being drawn by the proximal-end wire portions 38. On the other hand, the distal-end portions 37a of the intermediate wire portions 37 become farther from the longitudinal axis X of the sheath 10 in the directions perpendicular to the longitudinal axis X while being moved toward the proximal-end side along the longitudinal axis X by being drawn by the proximal-end wire portions 38. During this process, as a result of the loop portion 21 being deformed, the proximal-end side bend angle β formed between the intermediate wire portions 37 and the proximal-end wire portions 38 increases, and the distal-end side bend angle α formed between the distal-end wire portions 36 and the intermediate wire portions 37 decreases.

When portions of the proximal-end wire portions 38 of the loop portion 21 which correspond to ⅓ of the first length L are pulled into the sheath 10, the loop portion 21 that projects from the opening in the distal-end side of the sheath 10 becomes substantially lozenge-shaped (second state).

In the second state, the fourth opening width W4, which is the opening width of the loop portion 21 in the directions perpendicular to the longitudinal axis X of the sheath is in the range of 40% to 60% exclusive of the first width W1 of the loop portion 21.

In the second state, as a result of the loop portion 21 being deformed, the proximal-end side bend angle β formed between the intermediate wire portions 37 and the proximal-end wire portions 38 is of substantially 180 degrees, and the distal-end side bend angle α formed between the distal-end wire portions 36 and the intermediate wire portions 37 is of a minimum value. In the second state, the proximal-end portions 37b of the intermediate wire portions 37 are positioned outside of the sheath 10.

On the other hand, as illustrated in the right side of FIG. 4, with the existing endoscopic treatment tool that is free of the intermediate wire portions 37, when the snare wire is pulled in by approximately L/3 toward the proximal-end side, the opening width W7 of the loop portion of the snare wire is in the range of 30% to 35% of the width W1 of the loop. In other words, it can be confirmed that as a result of the snare wire that is free of the intermediate wire portions 37 being pulled approximately L/3 toward the proximal-end side, the opening width of the loop decreases abruptly.

As illustrated in FIG. 5, the surgeon places the loop portion 21 in the second state around the polyp P. Thereafter, as is the case with the large polyp P described hereinbefore, the surgeon passes a high-frequency electric current through the loop portion 21, excising the polyp P that is tightened by the loop portion 21. The surgeon may instead excise the polyp P by moving the loop portion 21 further toward the proximal-end side while the root of the polyp P is being tightened by the loop portion 21, without passing a high-frequency electric current through the loop portion 21.

According to the present embodiment, it has been illustrated that the surgeon places the loop portion 21 around the polyp P. The surgeon can appropriately adjust the opening width of the loop portion 21 in the range of the first width W1 to the fourth width W4 by pulling in the loop portion 21 in a manner to match the actual size of the polyp P.

Subsequently, the surgeon takes the excised polyp P out of the patient's body using a known tissue retrieval device, not illustrated, and pulls the endoscopic treatment tool 1 out of the body cavity, whereupon the treatment sequence is finished.

Advantages of Endoscopic Treatment Tool

With the endoscopic treatment tool 1 according to the present embodiment, in the loop portion 21, the length L in the longitudinal-axis directions is ranges from one and half times to two times the first opening width W1 of the loop portion 21, and the relationship: L1>L3>L2 is satisfied. With the endoscopic treatment tool 1 according to the present embodiment, in the loop portion 21, the length L1 of the proximal-end wire portions 38 ranges from 40% to 60% of the first length L of the loop portion 21.

With the existing endoscopic treatment tool, in a case where the length L of the loop portion is excessively large, when the loop portion is pushed out of the opening in the distal-end side of the endoscope, it is difficult to keep a sufficient amount of force for pressing the tissue.

Since polyps as targets to be excised are often circular in shape, the loop portion to be placed around the polyps should preferably be nearly circular in shape. According to the existing endoscopic snare disclosed in PTL 1, the portion of the loop portion on the proximal-end side thereof is very long, giving the loop portion a slender loop shape, as illustrated in FIGS. 9 and 10. Therefore, when the opening width of the snare loop is adjusted, a normal tissue not to be excised may possibly enter the snare loop. In a case where the loop portion is short, it is necessary to give the resilient wire a folding tendency to fold largely outwardly from the axial directions of the sheath of the endoscopic treatment tool in order to keep an opening width matching the size of the polyp P. In such a case, when the loop portion is placed around the polyp P and pulled into the sheath of the endoscopic treatment tool, the opening width of the loop portion may possibly decrease abruptly.

With the structure of the endoscopic treatment tool 1 according to the present embodiment, inasmuch as the length L of the loop portion 21 is restrained from being excessively large, when the loop portion 21 is pushed out of the opening in the distal-end side of the endoscope, it is possible to keep a necessary amount of force for pressing the tissue and also to form a nearly circular loop shape that matches the shape of the polyp P.

With this structure of the endoscopic treatment tool 1 according to the present embodiment, since the length L1 of the proximal-end wire portions 38 is larger than the length L3 of the distal-end wire portions 36, when the loop portion 21 is pulled into the sheath 10, the opening width of the loop portion 21 is prevented from decreasing abruptly. In other words, the endoscopic treatment tool 1 according to the present embodiment prevents the loop shape of the loop portion 21 from becoming narrower abruptly.

With the endoscopic treatment tool 1 according to the present embodiment, the length L2 of the intermediate wire portions 37 of the loop portion 21 ranges from 20% to 30% of the first width W1 of the loop portion 21.

With the endoscopic treatment tool 1 according to the present embodiment, as the distal-end portions 37a of the intermediate wire portions 37 are spaced from the longitudinal axis X of the sheath 10, they absorb part of a reduction in the opening width of the loop portion 21. Stated otherwise, the distal-end portions 37a of the intermediate wire portions 37 move to absorb a reduction in the distance or spreading between the pair of distal-end wire portions 36 as the opening width of the loop portion 21 decreases. As a consequence, as illustrated in FIG. 4, when the loop portion of the endoscopic treatment tool is pulled in toward the proximal-end side by the same length as with the endoscopic treatment tool that is free of the intermediate wire portions 37, the rate of reduction of the opening width of the loop portion 21 according to the present embodiment is made gradual compared with the endoscopic treatment tool that is free of the intermediate wire portions 37.

With the endoscopic treatment tool 1 according to the present embodiment, when the snare wire 20 is pulled in by approximately L/3, the fourth width W4 of the loop portion 21 is in the range of 40% to 60% exclusive of the first width W1 of the loop portion 21.

However, if the length L2 of the intermediate wire portions 37 according to the present embodiment is too large, then the first length L of the loop portion 21 is also large, resulting in a possibility that a tissue not to be excised may be excised. On the other hand, if the length L2 of the intermediate wire portions 37 is too small, then the effect of absorbing a reduction in the opening width of the loop portion 21 as described hereinbefore may not possibly be sufficiently achieved. Accordingly, the length L2 of the intermediate wire portions 37 according to the present embodiment should preferably be in the range of 20% to 30% of the first width W1 of the loop portion 21.

With the endoscopic treatment tool 1 according to the present embodiment being of the structure described hereinbefore, the first length L of the loop portion 21 can be reduced by approximately 30% in order to obtain the same first width W1, compared with the existing endoscopic treatment tool.

With the endoscopic treatment tool 1 according to the present embodiment, the distal-end side bend angle α is smaller than the proximal-end side bend angle β in the intermediate wire portions 37 of the loop portion 21. Since the endoscopic treatment tool 1 is of such a structure, the length L3 of the distal-end wire portions 36 is increased. As a result, when the loop portion 21 is pulled into the sheath 10, the rate of reduction of the opening width of the loop portion 21 becomes more gradual, so that the opening width of the loop portion 21 is likely to be maintained. Therefore, the surgeon finds it easy to adjust the opening width of the loop portion 21.

Modification 1

A first modification of the disclosed Technology will be described hereinafter with reference to FIGS. 6 and 7.

An endoscopic treatment tool according to the present modification is different from the embodiment described hereinbefore as to the structure of the loop portion of the snare wire.

In the description that follows, those components which are in common with those described hereinbefore will be denoted by identical numeral reference, and their redundant description will be omitted.

An endoscopic treatment tool 1A according to the present modification has a first bent portion 31A in place of the first bent portion 31 of the snare wire 20 of the endoscopic treatment tool 1 according to the embodiment described hereinbefore. As illustrated in FIG. 6, the endoscopic treatment tool 1A includes a snare wire 20A that includes a loop portion 21A having the first bent portion 31A, the pair of second bent portions 32, the pair of third bent portions 33, and the fourth bent portion 34.

Figure 6:
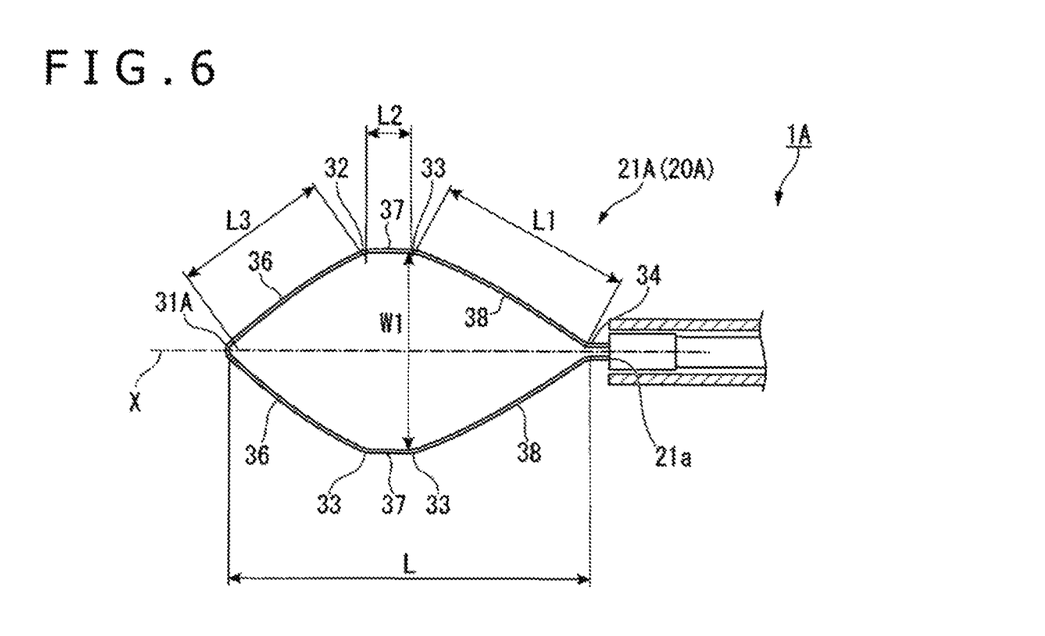
FIG. 6 is a view illustrating the structure of a snare loop of an endoscopic treatment tool according to a first modification of the disclosed Technology.

As illustrated in FIG. 6, the first bent portion 31A of the endoscopic treatment tool 1A according to the present modification is free of the protrusion 39 of the first bent portion 31 according to the embodiment described hereinbefore, but joins the pair of distal-end wire portions 36 at an acute angle. With the endoscopic treatment tool 1A according to the present modification, the distance from the fourth bent portion 34 on the proximal-end side to the first bent portion 31A on the distal-end side of the loop portion 21A along the longitudinal axis X of the sheath 10 is defined as a length, or first length, L of the loop portion 21A in the longitudinal-axis directions.

Figure 7:
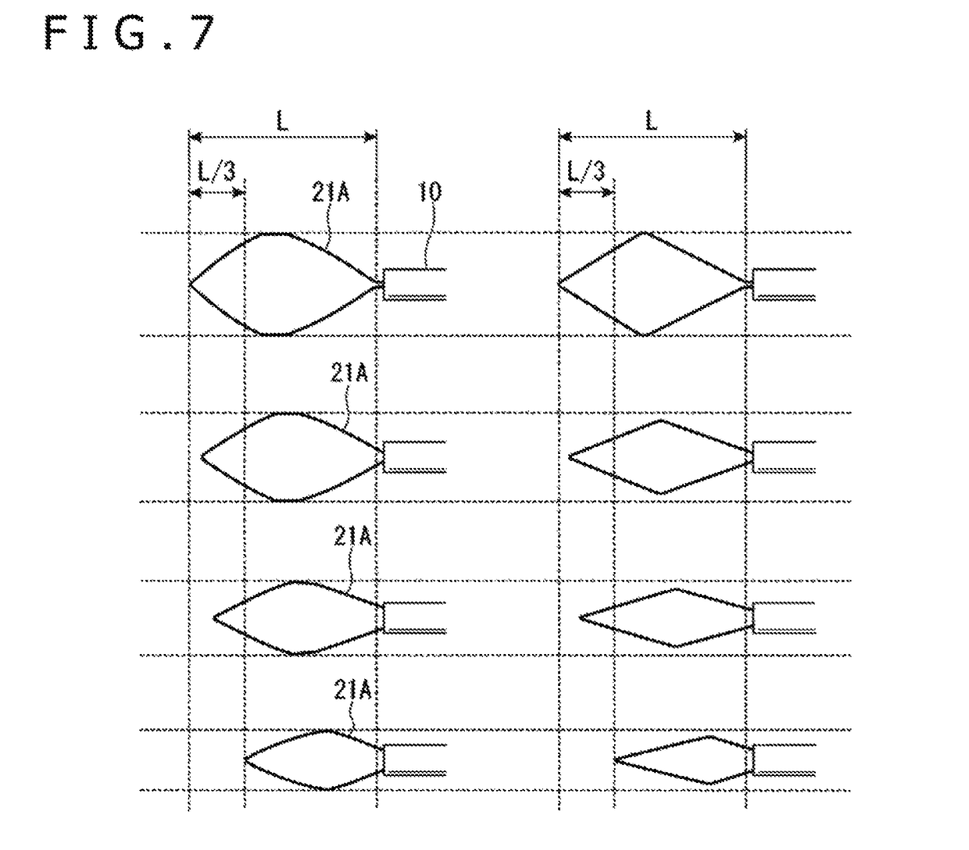
FIG. 7 a view illustrating the manner in which the endoscopic treatment tool according to the first modification of the disclosed Technology operates to pull part of the snare loop into a sheath.

As illustrated in a left side of FIG. 7, when the loop portion 21A according to the present modification projects completely from the opening in the distal end of the sheath 10, the length L of the loop portion 21A in the longitudinal-axis directions ranges from one and half times to two times the first opening width W1 of the loop portion 21A.

With the endoscopic treatment tool 1A according to the present modification, as with the endoscopic treatment tool 1 according to the embodiment described hereinbefore, the length L1 of the proximal-end wire portions 38, the length L2 of the intermediate wire portions 37, and the length L3 of the proximal-end wire portions 36 satisfy the relationship: L1>L3>L2. With the endoscopic treatment tool 1A according to the present modification, furthermore, the length L1 of the proximal-end wire portions 38 ranges from 40% to 60% of the length L of the loop portion 21A in the longitudinal-axis directions, and the length L2 of the intermediate wire portions 37 ranges from 20% to 30% of the first width W1 of the loop portion 21.

As illustrated in FIG. 7, when the loop portion 21A of the endoscopic treatment tool 1A is pulled in toward the proximal-end side by the same length as with the endoscopic treatment tool that is free of the intermediate wire portions 37, the rate of reduction of the opening width of the loop portion 21A is made gradual compared with the endoscopic treatment tool that is free of the intermediate wire portions 37. In other words, with the endoscopic treatment tool 1A according to the present modification, when the surgeon pulls the loop portion 21A into the sheath 10, the opening width of the loop portion 21A is restrained from being reduced abruptly.

Modification 2

Figure 8:
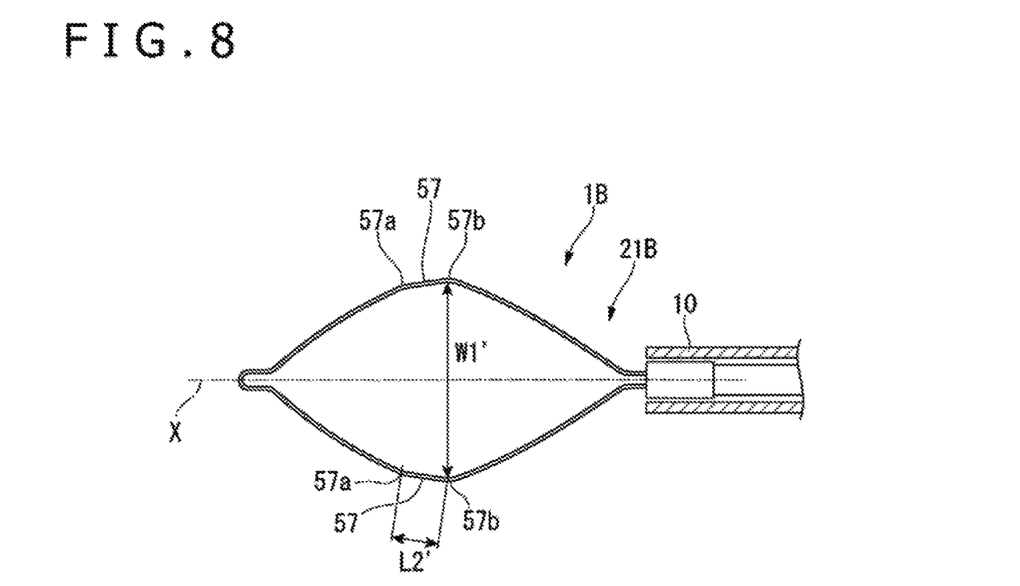
FIG. 8 is a view illustrating the structure of a snare loop of an endoscopic treatment tool according to a second modification of the disclosed Technology.

Modification 2 will be described hereinafter with reference to FIG. 8.

In the description that follows, those components which are in common with those described hereinbefore will be denoted by identical numeral reference, and their redundant description will be omitted.

In the embodiment described hereinbefore of the disclosed Technology, it has been illustrated that the pair of intermediate wire portions 37 lie substantially parallel to each other. As illustrated in FIG. 8, an endoscopic treatment tool 1B according to the present modification has a pair of intermediate wire portions 57 that lie out of parallel to each other.

Specifically, with the endoscopic treatment tool 1B according to the present modification, the pair of intermediate wire portions 57 are symmetrical with respect to the longitudinal axis X of the sheath 10. In the endoscopic treatment tool 1B according to the present modification, the pair of intermediate wire portions 57 extend outwardly from the longitudinal axis X of the sheath 10 in a direction from distal-end portions 57a toward proximal-end portions 57b. Stated otherwise, according to the present modification, in the pair of intermediate wire portions 57, the distance between the pair of proximal-end portions 57b is larger than the distance between the pair of distal-end portions 57a. According to the present modification, in the pair of intermediate wire portions 57, the distance between the pair of proximal-end portions 57b is defined as a maximum opening width, or first width, W1' of a loop portion 21B of the endoscopic treatment tool 1B.

With the endoscopic treatment tool 1B according to the present modification, as with the embodiment described hereinbefore of the disclosed Technology, the length L2' of the intermediate wire portions 57 ranges from 20% to 30% of the first width W1' of the loop portion 21B. Other structural details of the endoscopic treatment tool 1B according to the present modification may be the same as the structural details according to the embodiment described hereinbefore of the disclosed Technology.

With the endoscopic treatment tool 1B according to the present modification being of the structure described hereinbefore, as with the embodiment described hereinbefore of the disclosed Technology, when the loop portion 21B of the endoscopic treatment tool 1B is pulled toward the proximal-end side into the sheath 10, the opening width of the loop portion 21B is restrained from decreasing abruptly. With the endoscopic treatment tool 1B according to the present modification, furthermore, since the distance between the pair of proximal-end portions 57b is larger than the distance between the pair of distal-end portions 57a, when the loop portion 21B is pulled toward the proximal-end side into the sheath 10, the reduction in the opening width of the loop portion 21B is absorbed more appropriately.

Although the embodiment of the disclosed Technology has been described hereinbefore in detail with reference to the drawings, specific structural details are not limited to the embodiment, but may include design changes or the like without departing from the scope of the disclosed Technology.

The components illustrated in each of the embodiment and modifications described hereinbefore can be appropriately combined with each other. The disclosed Technology should not be limited by the description described hereinbefore, but should be limited only by the attached scope of claims for patent.

According to the embodiment described hereinbefore, there is provided an endoscopic treatment tool that allows the width of the opening of a snare loop thereof to be adjusted finely and that can excise a tissue as a target to be excised in an appropriate excision range and by an appropriate excision amount.

In sum, one aspect of the disclosed technology is directed to an endoscopic treatment tool comprises an elongated sheath and an elongated portion configured to be inserted in the elongated sheath and capable of being movable back and forth in directions along a longitudinal axis of the sheath. A loop portion is disposed on a distal end of the elongated portion and is constructed of a wire folded to form into a loop. The loop is variable in a size and a shape when the loop portion is moved into and out of the elongated sheath as the elongated portion being moved back and forth. The loop portion includes a first bent portion, a pair of second bent portions, a pair of third bent portions, and a fourth bent portion all of which are integrally formed from a distal end toward a proximal end of the loop portion. The pair of third bent portions and the fourth bent portion are joined to one another by proximal-end wire portions. The first bent portion and the pair of second bent portions are joined to one another by distal-end wire portions and in which length of the proximal-end wire portions is larger than length of the distal-end wire portions. The pair of second bent portions and the pair of third bent portions are joined to one another by intermediate wire portions and the length of the distal-end wire portions is larger than length of the intermediate wire portions. The loop portion projects maximally from the sheath when the elongated portion is moved back and forth. A first length that represents a length from the first bent portion to the fourth bent portion in the directions along the longitudinal axis ranges from one and half times to two times a first width that represents a maximum dimension of the loop portion in directions perpendicular to the longitudinal axis. The length of the proximal-end wire portions ranges from 40% to 60% of the first length and the length of the intermediate wire portions ranges from 20% to 30% of the first width of the loop portion.

In the endoscopic treatment tool when a portion of the loop portion which has ⅔ of the first length projects from the elongated sheath, a dimension of the loop portion in directions perpendicular to the longitudinal axis ranges from 40% to 60% exclusive of the first width. The loop portion has an intermediate position disposed on the intermediate wire portions in the directions along the longitudinal axis. In the loop portion, a distal-end side bend angle is formed between the distal-end wire portions and the intermediate wire portions is smaller than a proximal-end side bend angle formed between the intermediate wire portions and the proximal-end wire portions.

Another aspect of the disclosed technology is directed to an endoscopic treatment tool comprises an elongated sheath and an elongated portion configured to be inserted in the elongated sheath and capable of being movable back and forth in directions along a longitudinal axis of the elongated sheath. The loop portion is disposed on a distal end of the elongated portion and constructed of a wire folded to form into a loop. The loop being variable in a size and a shape when the loop portion being moved into and out of the sheath as the elongated portion being moved back and forth. The loop portion includes a first bent portion, a pair of second bent portions, a pair of third bent portions, and a fourth bent portion all of which being integrally formed from a distal end toward a proximal end of the loop portion. The pair of third bent portions and the fourth bent portion are joined to one another by proximal-end wire portions. The first bent portion and the pair of second bent portions are joined to one another by distal-end wire portions and length of the proximal-end wire portions is larger than length of the distal-end wire portions. The pair of second bent portions and the pair of third bent portions are joined to one another by intermediate wire portions and the length of the distal-end wire portions is larger than length of the intermediate wire portions and the loop portion projects maximally from the sheath and when the elongated portion is moved back and forth. The length of the proximal-end wire portions ranges from 40% to 60% of a first length and when a portion of the loop portion which has ⅔ of the first length projects from the sheath, a dimension of the loop portion in directions perpendicular to the longitudinal axis ranges from 40% to 60% exclusive of the first width of the loop portion.

In the endoscopic treatment tool when the loop portion projects maximally from the elongated sheath and when the elongated portion is moved back and forth, a first length that represents a length from the first bent portion to the fourth bent portion in the directions along the longitudinal axis ranges from one and half times to two times a first width that represents a maximum dimension of the loop portion in directions perpendicular to the longitudinal axis and the length of the intermediate wire portions ranges from 20% to 30% of the first width.

A further aspect of the disclosed technology is directed to an endoscopic treatment tool comprises an elongated sheath. An elongate portion configured to be inserted in the elongated sheath and capable of being movable back and forth in directions along a longitudinal axis of the sheath. A loop portion is disposed on a distal end of the elongated portion and constructed of a wire folded to form into a loop. The loop is variable in a size and a shape when the loop portion being moved into and out of the sheath as the elongated portion being moved back and forth. The loop portion includes a first bent portion, a pair of second bent portions, a pair of third bent portions, and a fourth bent portion all of which being integrally formed from a distal end toward a proximal end of the loop portion. The pair of third bent portions and the fourth bent portion are joined to one another by proximal-end wire portions. The first bent portion and the pair of second bent portions are joined to one another by distal-end wire portions and length of the proximal-end wire portions is larger than length of the distal-end wire portions. The pair of second bent portions and the pair of third bent portions are joined to one another by intermediate wire portions and the length of the distal-end wire portions is larger than length of the intermediate wire portions. The loop portion projects maximally from the sheath and when the elongated portion is moved back and forth, the length of the proximal-end wire portions ranges from 40% to 60% of a first length and in the loop portion, a distal-end bend angle is formed between the distal-end wire portions and the intermediate wire portions is smaller than a proximal-end side bend angle formed between the intermediate wire portions and the proximal-end wire portions.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:
1. An endoscopic treatment tool comprising:
   an elongated sheath;
   an elongated portion configured to be inserted in the elongated sheath and capable of being movable back and forth in directions along a longitudinal axis of the sheath; and
   a loop portion being disposed on a distal end of the elongated portion and constructed of a wire folded to form into a loop, the loop being variable in a size and a shape when the loop portion is moved into and out of the elongated sheath as the elongated portion is moved back and forth, wherein:
     the loop portion includes a first bent portion, a pair of second bent portions, a pair of third bent portions, and a fourth bent portion all of which being integrally formed from a distal end toward a proximal end of the loop portion, the pair of third bent portions and the fourth bent portion are joined to one another by proximal-end wire portions, the first bent portion and the pair of second bent portions are joined to one another by distal-end wire portions, a length of the proximal-end wire portions is larger than length of the distal-end wire portions, the pair of second bent portions and the pair of third bent portions are joined to one another by intermediate wire portions, the length of the distal-end wire portions is larger than length of the intermediate wire portions, and the loop portion projects maximally from the elongated sheath when the elongated portion is moved back and forth, a first length that represents a length from the first bent portion to the fourth bent portion in the directions along the longitudinal axis ranges from 1.5 times to 2 times a first width that represents a maximum dimension of the loop portion in directions perpendicular to the longitudinal axis, the length of the proximal-end wire portions ranges from 40% to 60% of the first length, and the length of the intermediate wire portions ranges from 20% to 30% of the first width of the loop portion.

2. The endoscopic treatment tool of claim 1, wherein, when a portion of the loop portion which has ⅔ of the first length projects from the sheath, a dimension of the loop portion in directions perpendicular to the longitudinal axis ranges from 40% to 60% exclusive of the first width.

3. The endoscopic treatment tool of claim 1, wherein the loop portion has an intermediate position disposed on the intermediate wire portions in the directions along the longitudinal axis.

4. The endoscopic treatment tool of claim 1, wherein in the loop portion, a distal-end side bend angle formed between the distal-end wire portions and the intermediate wire portions is smaller than a proximal-end side bend angle formed between the intermediate wire portions and the proximal-end wire portions.

5. An endoscopic treatment tool comprising:
an elongated sheath;
an elongated portion configured to be inserted in the elongated sheath and capable of being movable back and forth in directions along a longitudinal axis of the elongated sheath; and
a loop portion being disposed on a distal end of the elongated portion and constructed of a wire folded to form into a loop, the loop being variable in a size and a shape when the loop portion is moved into and out of the elongated sheath as the elongated portion is moved back and forth, wherein:
the loop portion includes a first bent portion, a pair of second bent portions, a pair of third bent portions, and a fourth bent portion all of which being integrally formed from a distal end toward a proximal end of the loop portion, the pair of third bent portions and the fourth bent portion are joined to one another by proximal-end wire portions, the first bent portion and the pair of second bent portions are joined to one another by distal-end wire portions and wherein length of the proximal-end wire portions is larger than a length of the distal-end wire portions, the pair of second bent portions and the pair of third bent portions are joined to one another by intermediate wire portions, and the length of the distal-end wire portions is larger than length of the intermediate wire portions, and the loop portion projects maximally from the sheath and when the elongated portion is moved back and forth, the length of the proximal-end wire portions ranges from 40% to 60% of a first length and when a portion of the loop portion which has ⅔ of the first length projects from the sheath, a dimension of the loop portion in directions perpendicular to the longitudinal axis ranges from 40% to 60% exclusive of the first width of the loop portion.

6. The endoscopic treatment tool of claim 5, wherein when the loop portion projects maximally from the sheath and when the elongate portion is moved back and forth, a first length that represents a length from the first bent portion to the fourth bent portion in the directions along the longitudinal axis ranges from 1.5 times to 2 times a first width that represents a maximum dimension of the loop portion in directions perpendicular to the longitudinal axis, and the length of the intermediate wire portions ranges from 20% to 30% of the first width of the loop portion.

7. An endoscopic treatment tool comprising:
an elongated sheath;
an elongate portion configured to be inserted in the elongated sheath and capable of being movable back and forth in directions along a longitudinal axis of the sheath; and
a loop portion being disposed on a distal end of the elongated portion and constructed of a wire folded to form into a loop, the loop being variable in a size and a shape when the loop portion is moved into and out of the sheath as the elongated portion is moved back and forth, wherein:
the loop portion includes a first bent portion, a pair of second bent portions, a pair of third bent portions, and a fourth bent portion all of which being integrally formed from a distal end toward a proximal end of the loop portion, the pair of third bent portions and the fourth bent portion are joined to one another by proximal-end wire portions, the first bent portion and the pair of second bent portions are joined to one another by distal-end wire portions and wherein length of the proximal-end wire portions is larger than length of the distal-end wire portions, the pair of second bent portions and the pair of third bent portions are joined to, and
by intermediate wire portions and wherein the length of the distal-end wire portions is larger than length of the intermediate wire portions, and the loop portion projects maximally from the sheath and when the elongated portion is moved back and forth, the length of the proximal-end wire portions ranges from 40% to 60% of a first length and in the loop portion, a distal-end bend angle formed between the distal-end wire portions and the intermediate wire portions is smaller than a proximal-end side bend angle formed between the intermediate wire portions and the proximal-end wire portions.

* * * * *